(12) United States Patent
Schick et al.

(10) Patent No.: US 11,597,799 B2
(45) Date of Patent: Mar. 7, 2023

(54) POLYESTER

(71) Applicant: BASF SE, Ludwigshafen (DE)

(72) Inventors: Michael Bernhard Schick, Ludwigshafen (DE); Motonori Yamamoto, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 688 days.

(21) Appl. No.: 16/609,233

(22) PCT Filed: May 2, 2018

(86) PCT No.: PCT/EP2018/061104
§ 371 (c)(1),
(2) Date: Oct. 29, 2019

(87) PCT Pub. No.: WO2018/206349
PCT Pub. Date: Nov. 15, 2018

(65) Prior Publication Data
US 2020/0190257 A1    Jun. 18, 2020

(30) Foreign Application Priority Data
May 10, 2017 (EP) .................................... 17170394

(51) Int. Cl.
| C08G 63/688 | (2006.01) |
| A61K 8/85 | (2006.01) |
| A61Q 5/06 | (2006.01) |
| C08G 18/08 | (2006.01) |
| C08G 18/32 | (2006.01) |
| C08G 18/34 | (2006.01) |
| C08G 18/38 | (2006.01) |
| C08G 18/73 | (2006.01) |
| C08G 63/78 | (2006.01) |
| C09J 167/02 | (2006.01) |

(52) U.S. Cl.
CPC ............ C08G 63/6886 (2013.01); A61K 8/85 (2013.01); A61Q 5/06 (2013.01); C08G 18/0828 (2013.01); C08G 18/3206 (2013.01); C08G 18/341 (2013.01); C08G 18/3855 (2013.01); C08G 18/73 (2013.01); C08G 63/78 (2013.01); C09J 167/02 (2013.01); C08G 2170/80 (2013.01)

(58) Field of Classification Search
None
See application file for complete search history.

(56) References Cited

U.S. PATENT DOCUMENTS

| 10,717,227 B2 | 7/2020 | Sawada et al. |
| 2005/0136025 A1 | 6/2005 | Pataut et al. |
| 2012/0322908 A1* | 12/2012 | Bastioli .................... C08L 67/02 521/182 |
| 2013/0101865 A1* | 4/2013 | Ren ........................ D21H 19/82 428/481 |
| 2018/0192477 A1 | 7/2018 | Klein et al. |
| 2020/0095372 A1 | 3/2020 | Yamamoto et al. |

FOREIGN PATENT DOCUMENTS

| CN | 102757552 A | 10/2012 |
| DE | 19943433 A1 | 3/2001 |
| WO | WO-2009/135921 A1 | 11/2009 |
| WO | WO-2010/077133 A1 | 7/2010 |
| WO | WO-2016/125860 A1 | 8/2016 |
| WO | WO-2017/023175 A1 | 2/2017 |
| WO | WO-2018/114215 A1 | 6/2018 |
| WO | WO-2018/206349 A1 | 11/2018 |

OTHER PUBLICATIONS

European Search Report for EP Patent Application No. 17170394.5, dated Nov. 8, 2017, 3 pages.
International Application No. PCT/EP2018/061104, International Search Report, dated Jul. 17, 2018.

* cited by examiner

*Primary Examiner* — Jeffrey D Washville
(74) *Attorney, Agent, or Firm* — Marshall, Gerstein & Borun LLP

(57) ABSTRACT

The present invention relates to a polyester consisting of (A) repeat units derived from an acid component, which consists of (a1) 2,5-furandicarboxylic acid, (a2) an aliphatic $C_4$-$C_{36}$ dicarboxylic acid or a mixture of a plurality of aliphatic $C_4$-$C_{36}$ dicarboxylic acids, and (a3) a sulfonate group-containing dicarboxylic acid, and of (B) repeat units derived from a di-ol/amine component, and optionally of further repeat units (C) and/or branching components (E), and of (D) repeat units derived from at least one di- or oligofunctional compound selected from the group consisting of a di- or oligoisocyanate and a di- or oligoisocyanurate. In addition, the present invention relates to the production of these polyesters and their use.

19 Claims, No Drawings

POLYESTER

CROSS-REFERENCE TO RELATED APPLICATIONS

This application is the U.S. National Stage application of International Patent Application No. PCT/EP2018/061104, filed May 2, 2018, which claims the benefit of European Patent Application No. 17170394.5, filed May 10, 2017.

The present invention relates to a polyester consisting of (A) repeat units derived from an acid component, which consists of (a1) 2,5-furandicarboxylic acid, (a2) an aliphatic $C_4$-$C_{36}$ dicarboxylic acid or a mixture of a plurality of aliphatic $C_4$-$C_{36}$ dicarboxylic acids, and (a3) a sulfonate group-containing dicarboxylic acid, and of (B) repeat units derived from a di-ol/amine component, and optionally of further repeat units (C) and/or branching components (E), and of (D) repeat units derived from at least one di- or oligofunctional compound selected from the group consisting of a di- or oligoisocyanate and a di- or oligoisocyanurate. In addition, the present invention relates to the production of these polyesters and their use.

Furandicarboxylic acid-containing aromatic polyesters are disclosed for example in WO 2010/077133 and furandicarboxylic acid-containing aliphatic-aromatic polyesters in WO 2009/135921. However, these polyesters are not soluble in water.

CN 102757552 discloses water-soluble furandicarboxylic acid-containing aromatic polyesters having a high content of a sulfonate group-containing compound of more than 12 mol % in the examples.

2,5-Furandicarboxylic acid can be produced from renewable raw materials. Polymers based on 2,5-furandicarboxylic acid are biodegradable in many cases. For many applications, water-soluble polymers are required. Water-soluble polymers based on 2,5-furandicarboxylic acid are disclosed in CN 102757552; in addition to 2,5-furandicarboxylic acid they also contain sodium sulfoisophthalate. However, the mechanical properties of these polymers are not good enough for many applications.

It is therefore an object of the present invention to provide water-soluble polymers based on 2,5-furandicarboxylic acid that have high mechanical strength values, for example a high yield stress, so that these polyesters are suitable for applications that require high mechanical strength values.

This object is achieved by the polyester as claimed in claim 1, which is a subject of the present invention. The subclaims describe special embodiments of the present invention.

The subsidiary claims, directed to products comprising the polyester according to the invention, uses comprising the polyester according to the invention, and a process for producing the polyesters according to the invention, are further subjects of the present invention.

The polyesters according to the invention are generally water-soluble. Compared with the polyesters disclosed in WO 2010/077133 and in WO 2009/135921, the polyesters according to the invention generally show higher biodegradability and improved mechanical properties such as increased tensile strength.

The invention is described in more detail below. In case of doubt, the following remarks relate only to particular embodiments of the present invention and do not restrict the subjects of the present invention.

The polyesters according to the invention comprise as a particular embodiment aromatic polyesters containing 100 mol %, based on components a1) and a2), of 2,5-furandicarboxylic acid and thus no component a2) and also aliphatic-aromatic polyesters containing 25 to 99 mol %, preferably 60 to 75 mol %, and especially preferably 65 to 75 mol %, in each case based on components a1) and a2), of 2,5-furandicarboxylic acid and accordingly 1 to 75 mol %, preferably 25 to 40 mol %, and especially preferably 25 to 35 mol % of an aliphatic $C_4$-$C_{36}$ dicarboxylic acid, in each case based on components a1) and a2).

2,5-Furandicarboxylic acid (component a1) is disclosed for example in WO 2009/135921.

In one embodiment, the 2,5-furandicarboxylic acid is employed in the polyester synthesis not as the free acid but as a di-$C_1$-$C_8$ alkyl ester, with diethyl 2,5-furandicarboxylate and in particular dimethyl 2,5-furandicarboxylate particularly preferred.

Particularly suitable as the aliphatic $C_4$-$C_{36}$ dicarboxylic acids (component a2) in the aliphatic-aromatic polyesters are α,ω-$C_4$-$C_{36}$ dicarboxylic acids including, for example, succinic acid, glutaric acid, adipic acid, suberic acid, azelaic acid, sebacic acid, a 1,12-$C_{12}$ dicarboxylic acid, brassylic acid, 1,16-$C_{16}$ dicarboxylic acid, 1,18-$C_{18}$ dicarboxylic acid or 1,36-$C_{36}$ dicarboxylic acid or mixtures of these dicarboxylic acids. Preference is given to succinic acid, glutaric acid, adipic acid, azelaic acid, sebacic acid or a 1,12-$C_{12}$ dicarboxylic acid or mixtures thereof and especial preference to succinic acid, adipic acid or sebacic acid or mixtures thereof.

Particularly suitable as the sulfonate group-containing dicarboxylic acid (component a3) are aromatic sulfonic acids and salts thereof, with alkali metal salts thereof especially preferred. These include for example 1,4-benzenedicarboxylic acid-2-sulfonic acid, 1,3-benzenedicarboxylic acid-5-sulfonic acid hereinafter also referred to as isophthalic acid-5-sulfonic acid-, 1,2-benzenedicarboxylic acid-3-sulfonic acid, 1,2-benzenedicarboxylic acid-4-sulfonic acid and salts thereof and especially preferably alkali metal salts thereof. Isophthalic acid-5-sulfonic acid sodium salt (NaSiP for short) is particularly preferred.

Among both the above-described aromatic polyesters and the aliphatic-aromatic polyesters, preference is given to those comprising 10 to 60 mol %, preferably 15 to 40 mol %, based on components a1) to a3), of a sulfonate group-containing dicarboxylic acid and particular preference to isophthalic acid-5-sulfonic acid sodium salt, as these are suitable for forming aqueous solutions.

Suitable diols (component b1) include aliphatic $C_2$-$C_{12}$ diols such as ethylene glycol, 1,2-propanediol, 1,3-propanediol, 1,2-butanediol, 1,4-butanediol, 1,5-pentanediol, 2,4-dimethyl-2-ethylhexane-1,3-diol, 2,2-dimethyl-1,3-propanediol, 2-ethyl-2-butyl-1,3-propanediol, 2-ethyl-2-isobutyl-1,3-propanediol, 1,6-hexanediol, 1,8-octanediol, and 2,2,4-trimethyl-1,6-hexanediol, with ethylene glycol, 1,3-propanediol, 1,4-butanediol, and 2,2-dimethyl-1,3-propanediol (neopentyl glycol) preferred. The latter also have the advantage of being obtainable as a renewable raw material. Mixtures of different alkanediols may also be employed.

Preferred aromatic polyesters according to the invention are those that comprise ethylene glycol or cyclohexanedimethanol as the diol component or instead of b1) comprise diethylene glycol or triethylene glycol as component b2), and preferred aliphatic-aromatic polyesters according to the invention are in particular those comprising 1,4-butanediol as the diol component.

Suitable diols (component b1) also include cycloaliphatic $C_6$-$C_{12}$ diols such as cyclopentanediol, 1,4-cyclohexanediol, 1,4-cyclohexanedimethanol (cis/trans), 1,4-di(hydroxymethyl)cyclohexane or 2,5-tetrahydrofurandimethanol, with 1,4-cyclohexanedimethanol preferred.

In one embodiment, the polyesters according to the invention comprise, as component E, 0 to 4% by weight, preferably 0.01 to 1.0% by weight, and especially preferably 0.05 to 0.3% by weight, based on the sum of components A, B, and C, of a branching component having at least 3 functional groups (component E). The branching component is preferably an at least trifunctional alcohol or an at least trifunctional carboxylic acid.

Particularly preferred branching components have three to six functional groups. Examples include: tartaric acid, citric acid, malic acid, trimethylolpropane, trimethylolethane, pentaerythritol, polyether triols and glycerol, trimesic acid, trimellitic acid, trimellitic anhydride, pyromellitic acid, and pyromellitic dianhydride. Preference is given to polyols such as trimethylolpropane, pentaerythritol, and especially glycerol. This component makes it possible to construct biodegradable polyesters that have structural viscosity. These biodegradable polyesters are easier to process.

Component b2 comprises a dihydroxy compound with ether functions of formula I

HO—[(CH$_2$)$_n$—O]$_m$—H    (I)

in which n is 2, 3 or 4 and m is an integer from 2 to 250.

Suitable dihydroxy compounds include diethylene glycol, triethylene glycol, polyethylene glycol, polypropylene glycol, and polytetrahydrofuran (polyTHF), particularly preferably diethylene glycol, triethylene glycol, and polyethylene glycol, it also being possible to employ mixtures thereof or compounds having differing variables n (see formula I), for example polyethylene glycol which contains propylene units (n=3), obtainable for example by polymerization according to methods known per se initially of ethylene oxide and subsequently with propylene oxide, particularly preferably a polymer based on polyethylene glycol having differing variables n, in which units formed from ethylene oxide predominate.

The chosen molecular weight ($M_n$) of the polyethylene glycol is generally in the range from 250 to 8000, preferably from 600 to 3000 g/mol.

The following may be employed as the hydroxycarboxylic acid c1): glycolic acid, D-, L- or D,L-lactic acid, 6-hydroxyhexanoic acid, cyclic derivatives thereof such as glycolide (1,4-dioxane-2,5-dione), D- or L-dilactide (3,6-dimethyl-1,4-dioxane-2,5-dione), p-hydroxybenzoic acid and also their oligomers and polymers such as 3-polyhydroxybutyric acid, polyhydroxyvaleric acid, polylactic acid (for example the products marketed by NatureWorks under the trade name Ingeo®) and also a mixture of 3-polyhydroxybutyric acid and 4-polyhydroxybutyrates or 3-polyhydroxyvaleric acid or 3-polyhydroxyhexanoic acid, the low-molecular-weight and cyclic derivatives thereof being particularly preferable for the production of polyesters.

The hydroxycarboxylic acids may be employed for example in amounts from 0.01 to 50% by weight, preferably from 0.1 to 30% by weight, based on the amount of A and B.

Preferably employed as the amino $C_2$-$C_{12}$ alkanol or amino $C_5$-$C_{10}$ cycloalkanol (component b3), with this defined as also including 4-aminomethylcyclohexanemethanol, are amino $C_2$-$C_6$ alkanols such as 2-aminoethanol, 3-aminopropanol, 4-aminobutanol, 5-aminopentanol, 6-aminohexanol, and amino $C_5$-$C_6$ cycloalkanols such as aminocyclopentanol and aminocyclohexanol or mixtures thereof.

Preferably employed as the diamino $C_1$-$C_8$ alkane (component b4) are diamino $C_4$-$C_6$ alkanes such as 1,4-diaminobutane, 1,5-diaminopentane, and 1,6-diaminohexane (hexamethylenediamine, "HMD").

c2 is preferably an aminocarboxylic acid selected from the group consisting of caprolactam, 1,6-aminocaproic acid, laurolactam, 1,12-aminolauric acid, and 1,11-aminoundecanoic acid Employable as component c2 are aminocarboxylic acids selected from the group consisting of caprolactam, 1,6-aminocaproic acid, laurolactam, 1,12-aminolauric acid, and 1,11-aminoundecanoic acid.

c2 is generally employed in amounts of 0 to 20% by weight, preferably of 0.1 to 10% by weight, based on the total amount of components A and B.

Normally employed as component D is an isocyanate or isocyanurate or a mixture of different isocyanates and isocyanurates. Employable isocyanates are aromatic or aliphatic diisocyanates. However, it is also possible to employ higher-functional isocyanates.

In the context of the present invention, an aromatic diisocyanate is understood as meaning especially tolylene 2,4-diisocyanate, tolylene 2,6-diisocyanate, 2,2'-diphenylmethane diisocyanate, 2,4'-diphenylmethane diisocyanate, 4,4'-diphenylmethane diisocyanate, naphthylene 1,5-diisocyanate or xylylene diisocyanate.

Of these, 2,2'-, 2,4'-, and 4,4'-diphenylmethane diisocyanate are particularly preferred. The latter diisocyanates are generally employed as mixtures.

As a triaryl isocyanate, tris(4-isocyanatophenyl)methane may also be considered. The polyaryl aromatic diisocyanates are generated for example in the production of monoaryl or diaryl diisocyanates.

Component d1 may also contain minor amounts, for example up to 5% by weight based on the total weight of component D, of uretdione groups, for example for capping the isocyanate groups.

In the context of the present invention, an aliphatic diisocyanate D is understood as meaning, especially, straight-chain or branched alkylene diisocyanates or cycloalkylene diisocyanates having 2 to 20 carbon atoms, preferably 3 to 15 carbon atoms, for example 1,6-hexamethylene diisocyanate, isophorone diisocyanate or methylenebis(4-isocyanatocyclohexane). Particularly preferred aliphatic diisocyanates D are isophorone diisocyanate and in particular 1,6-hexamethylene diisocyanate.

Preferred isocyanurates include aliphatic isocyanurates derived from alkylene diisocyanates or cycloalkylene diisocyanates having 2 to 20 carbon atoms, preferably 3 to 15 carbon atoms, for example isophorone diisocyanate or methylenebis(4-isocyanatocyclohexane). The alkylene diisocyanates may be either straight-chain or branched. Particular preference is given to isocyanurates based on n-hexamethylene diisocyanate, for example cyclic trimers, pentamers or higher oligomers of 1,6-hexamethylene diisocyanate.

Component D is generally employed in amounts of 0.1 to 4% by weight, preferably 0.2 to 1.2% by weight, based on components A and B and optionally C.

Aromatic polyesters according to the invention may comprise 100 mol %, based on components a1) and a2), of 2,5-furandicarboxylic acid and thus no component a2). Aromatic polyesters comprise for example: poly(alkylene-2,5-furandicarboxylates) such as poly(ethylene-2,5-furandicarboxylate), poly(propylene-2,5-furandicarboxylate), poly(butylene-2,5-furandicarboxylate), poly(hexylene-2,5-furandicarboxylate), poly(octylene-2,5-furandicarboxylate), or poly(alkoxylene-2,5-furandicarboxylates) such as poly (ethoxyethylene-2,5-furandicarboxylates) or poly(diethoxyethylene-2,5-furandicarboxylates).

Aliphatic-aromatic polyesters according to the invention comprise preferably 25 to 99 mol %, more preferably 60 to 75 mol %, and especially preferably 65 to 75 mol % of a 2,5-furandicarboxylic acid and accordingly 1 to 75 mol %, preferably 25 to 40 mol %, and especially preferably 25 to 35 mol % of an aliphatic $C_4$-$C_{36}$ dicarboxylic acid, based on the sum of components a1) and a2). Aliphatic-aromatic polyesters comprise in particular: polybutylene-2,5-furandicarboxylate-co-adipate, polybutylene-2,5-furandicarboxylate-co-azelate, polybutylene-2,5-furandicarboxylate-co-sebacate, polybutylene-2,5-furandicarboxylate-co-brassylate, polybutylene-2,5-furandicarboxylate-co-1,12-$C_{12}$-dicarboxylate, polybutylene-2,5-furandicarboxylate-co-1,18-$C_{18}$-dicarboxylate, and polybutylene-2,5-furandicarboxylate-co-1,36-$C_{36}$-dicarboxylate.

The viscosity number of the polyesters according to the invention according to EN-ISO 1628-1:2012-10 (measured as a 0.05 g/ml solution in phenol/o-dichlorobenzene (1:1)) is preferably between 50 and 450, more preferably from 70 to 250 ml/g (measured in o-dichlorobenzene/phenol (50/50 weight/weight)). The melting point is preferably in the range from 85 to 150° C., more preferably in the range from 95 to 140° C.

In the meaning of the present invention, the feature "biodegradable" is satisfied for a substance or a substance mixture if this substance or the substance mixture shows a percentage biodegradation according to DIN EN 13432 of at least 90%.

Biodegradability generally results in the polyester (mixtures) breaking down within an appropriate and verifiable timeframe. Degradation can take place enzymatically, hydrolytically, oxidatively, and/or by the action of electromagnetic radiation, for example UV radiation, and is for the most part brought about by the action of microorganisms such as bacteria, yeasts, fungi, and algae. Biodegradability is quantifiable, for example, by mixing polyesters with compost and storing them for a certain time. For example, according to DIN EN 13432, $CO_2$-free air is passed through matured compost during composting and said compost is subjected to a defined temperature program. Biodegradability is defined here as the percentage biodegradation, via the ratio of the net $CO_2$ release from the sample (after subtracting the $CO_2$ released by the compost without sample) to the maximum $CO_2$ release from the sample (calculated from the carbon content of the sample). Biodegradable polyester (mixtures) generally show clear signs of degradation such as fungus growth and tear and hole formation after just a few days of composting.

Other methods for determining biodegradability are described for example in ASTM D 5338 and ASTM D 6400 and in OECD 301.

The polyesters and polyester mixtures according to the invention may preferably comprise the following fillers.

Calcium carbonate may be employed for example at 10 to 25% by weight, preferably 10 to 20% by weight, particularly preferably 12 to 28% by weight, based on the total weight of the polymer mixture. Calcium carbonate from Omya, inter alia, has proven suitable. The calcium carbonate generally has a mean particle size of 0.5 to 10 micrometers, preferably 1-5 and particularly preferably 1-2.5 micrometers.

Talc may be employed for example at 3 to 15% by weight, preferably 5 to 10% by weight, particularly preferably 5 to 8% by weight, based on the total weight of the polymer mixture. Talc from Mondo Minerals, inter alia, has proven suitable. The talc generally has a mean particle size of 0.5-10, preferably 1-8, particularly preferably 1-3 micrometers.

Yet further minerals that may be present in addition to the fillers calcium carbonate and talc include: graphite, gypsum, carbon black, iron oxide, calcium chloride, kaolin, silica (quartz), sodium carbonate, titanium dioxide, silicate, wollastonite, mica, montmorillonites, mineral fibers, and natural fibers.

Natural fibers generally include cellulose fibers, kenaf fibers, hemp fibers, wood flour, and potato peelings. These are preferably employed at 1 to 20% by weight based on the polymer mixture.

The minerals including the fillers calcium carbonate and talc may also be employed as nanofillers. Nanofillers are, in particular, finely divided phyllosilicates, preferably argillaceous minerals, particularly preferably montmorillonite containing argillaceous minerals, the surface of which has been modified with one or more quaternary ammonium salts and/or phosphonium salts and/or sulfonium salts. Preferred argillaceous minerals are natural montmorillonites and bentonites.

Fillers may overall be added to the polyester mixtures for example at 10 to 35% by weight based on the total weight of the polymer mixture.

The polyesters according to the invention may be employed for setting hair, also termed hair styling. For this, the polyesters according to the invention may be employed as a component of formulations that otherwise comprise constituents familiar to a person skilled in the art that are suitable for hair styling formulations.

EXAMPLES

Designations, Abbreviations, and Molar Masses M (in g/mol)
  2,5-FDCA 2,5-Furandicarboxylic acid
  2,5-FDCA-DME 2,5-Furandicarboxylic acid dimethyl ester, M=184 g/mol (also: dimethyl furandicarboxylate)
  NaSIP Sodium sulfoisophthalate; structural formula:

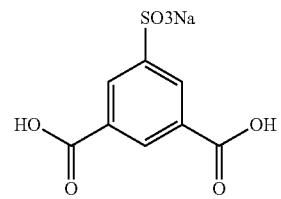

DMNaSIP Sodium dimethyl sulfoisophthalate; M=296 g/mol (also: dimethyl sodium sulfoisophthalate)
  HDI Hexamethylene diisocyanate
  EG Ethylene glycol, M=62 g/mol
  DEG Diethylene glycol; M=106 g/mol
  BD 1,4-Butanediol; M=90 g/mol
  1,8-Octanediol M=146 g/mol
  Triethylene glycol M=150 g/mol
  Tetraethylene glycol M=194 g/mol
Test Methods The properties of the polyesters produced according to the examples were tested using the following methods: Where reference is made here to standards, this in each case refers to the version of the standard that was in force on 1 Aug. 2016.

Viscosity numbers VN were determined according to EN-ISO 1628-1:2012-10, capillary viscometry. An Ubbelohde M-II microviscometer was used. The solvent used was a phenol/o-dichlorobenzene mixture (50/50 weight/weight).

The elastic modulus and the yield stress were determined according to ISO 527-3: 2003 by a tensile test using tensile bars with a thickness of approximately 420 μm.

The glass transition temperature Tg was determined according to DIN EN ISO 11357-3:2913-04.

General Method of Production of the Polyesters

The mol % values shown hereinafter are based on the sum of the moles of dimethyl furandicarboxylate and dimethyl sodium sulfoisophthalate, which is set at 100 mol %.

For the production of the polyesters, 70 mol % of dimethyl 2,5-furandicarboxylate, 30 mol % of dimethyl sodium sulfoisophthalate, 130 mol % of the specified diol, and the amount of glycerol optionally specified were mixed with the specified amount of tetrabutyl orthotitanate (TBOT). The reaction mixture was heated to a temperature of 180° C. and reacted at this temperature for 2 h. The temperature was then increased to 240° C. and the excess diol was distilled off under vacuum over a period of 1-2 h. The optionally specified amount of hexamethylene diisocyanate was then added slowly over 10 min at 240° C.

In this process, the TBOT acts as a catalyst for the polycondensation. Glycerol serves as a branching component and HDI as a "chain extender". On addition of HDI, the polyester chains present react with the HDI through their terminal OH groups and form urethane groups. This increases the mean molar mass of the polyester.

Process for Production of the Polyesters According to the Examples

Polyesters were produced according to the general method of production of the polyesters. The substances shown below were used. The polyesters obtained had the specified properties (Tg, VN, elastic modulus, yield stress). The amounts of glycerol and HDI are given in g and in % by weight, where % by weight refers to the sum of the masses of the repeat units derived from 2,5-FDCA, NaSIP, and the diol employed, which was set at 100%.

Example 1-1

2,5-FDCA-DME: 64.3 g (0.35 mol) (70 mol %)
DMNaSIP: 44.3 g (0.15 mol) (30 mol %)
Ethylene glycol: 40.3 g (0.65 mol) (130 mol %)
Glycerol: 0.11 g (0.1% by weight) (0.0012 mol)
TBOT: 0.08 g
HDI: 0.86 g (0.8% by weight) (0.0051 mol)
Tg: 84° C., VN: 80, elastic modulus: 2950 MPa, yield stress: 65 MPa Example 1-2

2,5-FDCA-DME: 64.3 g (0.35 mol) (70 mol %)
DMNaSIP: 44.3 g (0.15 mol) (30 mol %)
Ethylene glycol: 40.3 g (0.65 mol) (130 mol %)
TBOT: 0.08 g
HDI: 0.86 g (0.8% by weight)
Tg: 82° C., VN: 76, elastic modulus: 2900 MPa, yield stress: 60 MPa Comparative Example 1

This is a comparative example. It is not in accordance with the invention, as it contains neither HDI nor glycerol.
2,5-FDCA-DME: 64.3 g (0.35 mol) (70 mol %)
DMNaSIP: 44.3 g (0.15 mol) (30 mol %)
Ethylene glycol: 40.3 g (0.65 mol) (130 mol %)
TBOT: 0.08 g
Tg: 80° C., VN: 35, elastic modulus: 2900 MPa, yield stress: 35 MPa Example 2

2,5-FDCA-DME: 54.0 g (0.293 mol) (70 mol %)
DMNaSIP: 37.2 g (0.125 mol) (30 mol %)
Diethylene glycol: 57.8 g (0.545 mol) (130 mol %)
Glycerol: 0.11 g (0.1% by weight)
TBOT: 0.08 g
HDI: 0.87 g (0.8% by weight)
Tg: 61° C., VN: 85

Comparative Example 2

This is a comparative example. It is not in accordance with the invention, as it contains neither HDI nor glycerol.
2,5-FDCA-DME: 54.0 g (0.293 mol) (70 mol %)
DMNaSIP: 37.2 g (0.125 mol) (30 mol %)
Diethylene glycol: 57.8 g (0.545 mol) (130 mol %)
TBOT: 0.08 g
Tg: 61° C., VN: 43

Example 3

2,5-FDCA-DME: 57.3 g (0.31 mol) (70 mol %)
DMNaSIP: 39.5 g (0.13 mol) (30 mol %)
1,4-Butanediol: 52.1 g (0.58 mol) (130 mol %)
Glycerol: 0.11 g (0.1% by weight)
TBOT: 0.08 g
HDI: 0.87 g (0.8% by weight)
Tg: 57° C., VN: 73

Example 4

2,5-FDCA-DME: 47.1 g (0.256 mol) (70 mol %)
DMNaSIP: 32.5 g (0.11 mol) (30 mol %)
1,8-Octanediol: 69.4 g (0.475 mol) (130 mol %)
Glycerol: 0.11 g (0.1% by weight)
TBOT: 0.08 g
HDI: 0.88 g (0.8% by weight)
Tg: 6° C., VN: 83

Example 5

2,5-FDCA-DME: 46.5 g (0.253 mol) (70 mol %)
DMNaSIP: 32.1 g (0.108 mol) (30 mol %)
Triethylene glycol: 70.4 g (0.469 mol) (130 mol %)
Glycerol: 0.11 g (0.1% by weight)
TBOT: 0.08 g
HDI: 0.88 g (0.8% by weight)
Tg: 29° C., VN: 78

Example 6

2,5-FDCA-DME: 40.8 g (0.2217 mol) (70 mol %)
DMNaSIP: 28.1 g (0.095 mol) (30 mol %)
Tetraethylene glycol: 80.0 g (0.41 mol) (130 mol %)
Glycerol: 0.11 g (0.1% by weight)
TBOT: 0.08 g
HDI: 0.88 g (0.8% by weight)
Tg: 14° C., VN: 75

Composition of the Polyesters Produced

The values in mol % are based on the sum of the repeat units derived from 2,5-FDCA and from Na-SIP. This sum was set at 100 mol %. All polyesters comprised:

70 mol % of repeat units derived from 2,5-FDCA
30 mol % of repeat units derived from NaSIP
100 mol % of repeat units derived from the respective diol (the excess of the 130% initially present was distilled off).
Additional repeat units derived from glycerol and/or repeat units derived from HDI, if present. Repeat units derived from glycerol are at the expense here of repeat units derived from the diol employed, the content of which in the polyester is thus, strictly speaking, slightly below 100 mol % if glycerol is used. Since the amount of glycerol used was low, this was not included in the values for the number of repeat units derived from the diol.

Values in mol %, where not stated in % by weight; E=example, CE=comparative example

| Repeat units derived from: | E 1-1 [mol %] | E 1-2 | CE 1 | E 2 |
|---|---|---|---|---|
| 2,5-FDCA | 70 | 70 | 70 | 70 |
| NaSIP | 30 | 30 | 30 | 30 |
| 1,4-Butane-diol | — | — | — | — |
| Ethylene glycol | 100 | 100 | 100 | — |
| Diethylene glycol | — | — | — | 100 |
| Triethylene glycol | — | — | — | — |
| Tetraethylene glycol | — | — | — | — |
| 1,8-Octanediol | — | — | — | — |
| Glycerol | 0.1% by weight | — | — | 0.1% by weight |
| HDI | 0.8% by weight | 0.8% by weight | — | 0.8% by weight |

| Repeat units derived from: | CE 2 [mol %] | E 3 | E 4 | E 5 |
|---|---|---|---|---|
| 2,5-FDCA | 70 | 70 | 70 | 70 |
| NaSIP | 30 | 30 | 30 | 30 |
| 1,4-Butanediol | — | 100 | — | — |
| Ethylene glycol | — | — | — | — |
| Diethylene glycol | 100 | — | — | — |
| Triethylene glycol | — | — | — | 100 |
| Tetraethylene glycol | — | — | — | — |
| 1,8-Octanediol | — | — | 100 | — |
| Glycerol | — | 0.1% by weight | 0.1% by weight | 0.1% by weight |
| HDI | — | 0.8% by weight | 0.8% by weight | 0.8% by weight |

| Repeat units derived from: | E 6 [mol %] |
|---|---|
| 2,5-FDCA | 70 |
| NaSIP | 30 |
| 1,4-Butane-diol | — |
| Ethylene glycol | — |
| Diethylene glycol | — |
| Triethylene glycol | — |
| Tetraethylene glycol | 100 |
| 1,8-Octanediol | — |
| Glycerol | 0.1% by weight |
| HDI | 0.8% by weight |

The glass transition temperature Tg of the polyesters is clearly dependent on the diol employed.

The values for VN (viscosity number, a measure of the mean molar mass (weight average) of the polyesters) and for the yield stress are considerably lower for the comparative examples than for the examples according to the invention. The polyesters in the examples according to the invention thus have a higher mean molar mass (weight average) Mw and a higher mechanical strength.

The invention claimed is:
1. A polyester consisting of:
A) repeat units derived from an acid component, which consists of
   a1) 30 to 90 mol %, based on the sum of components a1, a2, and a3, of 2,5-furandicarboxylic acid,
   a2) 0 to 60 mol %, based on the sum of components a1, a2, and a3, of an aliphatic $C_4$-$C_{36}$ dicarboxylic acid or a mixture of a plurality of aliphatic $C_4$-$C_{36}$ dicarboxylic acids, and
   a3) 10 to 60 mol %, based on the sum of components a1, a2, and a3, of a sulfonate group-containing dicarboxylic acid,
   wherein a3 is an aromatic sulfonate group-containing dicarboxylic acid in which the sulfonate group is present either as the free acid or as a salt, and a3 is selected from the group consisting of 1,4-benzenedicarboxylic acid-2-sulfonic acid, 1,3-benzenedicarboxylic acid-5-sulfonic acid, 1,2-benzenedicarboxylic acid-3-sulfonic acid, and 1,2-benzenedicarboxylic acid-4-sulfonic acid, in each case in the form of the free acid or of a salt, and
   wherein the molar percentages of components a1) to a3) together add up to 100 mol %,
B) repeat units derived from a di-ol/amine component consisting of
   b1) a $C_2$ to $C_{12}$ alkanediol or a mixture of a plurality of $C_2$ to $C_{12}$ alkanediols, and/or
   b2) a dihydroxy compound of formula I,

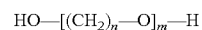

$$HO-[(CH_2)_n-O]_m-H \qquad (I)$$

where n is 2, 3 or 4 and m is an integer from 2 to 250, or a mixture of a plurality of such dihydroxy compounds,
b3) optionally one or more amino $C_2$ to $C_{12}$ alkanols or one or more amino $C_5$ to $C_{10}$ cycloalkanols or mixtures thereof, and
b4) optionally one or more diamino $C_1$ to $C_8$ alkanes,
wherein the amount of B is chosen so that for every 100 mol of A there is 100 mol of B present, minus the number of moles of D and E,
and wherein a sum of b1 and b2 in B is at least 50 mol %,
C) optionally repeat units derived from
c1) one or more hydroxycarboxylic acids of formula IIa,

where G represents a radical selected from the group consisting of phenylene, $-(CH_2)_q-$, in which q is an integer from 1 to 5, $-C(R)H-$, and $-C(R)HCH_2-$, in which R is methyl or ethyl, and/or
c2) one or more aminocarboxylic acids or cyclic amides thereof selected from the group consisting of caprolactam, 1,6-aminocaproic acid, laurolactam, 1,12-aminolauric acid, and 1,11-aminoundecanoic acid,
wherein the proportion of C in the total mass of the polyester is not more than 20% by weight,
D) 0.1 to 4% by weight, based on the sum of components A, B, and C, of repeat units derived from at least one di- or oligofunctional compound selected from the group consisting of a di- or oligoisocyanate and a di- or oligoisocyanurate, and
E) 0.1 to 4% by weight, based on the sum of components A, B, and C, of repeat units derived from a branching component that contains at least three functional groups, wherein the functional groups are selected from the group consisting of COOH, OH, $NH_2$, and mixtures thereof.

2. The polyester as claimed in claim 1, wherein a sum of a2, b3, b4, c1, and c2, based on the total mass of the polyester, is not more than 10% by weight.

3. The polyester as claimed in claim 1, wherein b1 is selected from the group consisting of ethylene glycol, 1,2-propanediol, 1,3-propanediol, 1,2-butanediol, 1,4-butanediol, 1,5-pentanediol, 2,4-dimethyl-2-ethylhexane-1,3-diol, 2,2-dimethyl-1,3-propanediol, 2-ethyl-2-butyl-1,3-propanediol, 2-ethyl-2-isobutyl-1,3-propanediol, 1,6-hexanediol, 1,8-octanediol, and 2,2,4-trimethyl-1,6-hexanediol.

4. The polyester as claimed in claim 1, wherein b2 is selected from the group consisting of diethylene glycol, triethylene glycol, tetraethylene glycol, polyethylene glycol, polypropylene glycol, and polytetrahydrofuran.

5. The polyester as claimed in claim 1, wherein D is repeat units derived from an aliphatic diisocyanate, wherein the diisocyanate is a straight-chain or branched alkylene diisocyanate or cycloalkylene diisocyanate having in both cases 2 to 20 carbon atoms.

6. The polyester as claimed in claim 1, wherein E is repeat units derived from a branching component selected from the group consisting of tartaric acid, citric acid, malic acid, trimethylolpropane, trimethylolethane, pentaerythritol, a polyether triol, glycerol, trimesic acid, trimellitic acid, and pyromellitic acid.

7. An aqueous solution comprising the polyester as claimed in claim 1 and water.

8. A personal care formulation comprising the polyester as claimed in claim 1 and water.

9. A laminating adhesive comprising the polyester as claimed in claim 1 and water.

10. A method of setting hair comprising contacting the hair with a personal care formulation comprising the polyester as claimed in claim 1 and water.

11. A process for production of the polyester as claimed in claim 1 comprising
the reaction of a mixture comprising the acid component as defined under A, the di-ol/amine component as defined under B, optionally the hydroxycarboxylic acids as defined under c1, optionally the aminocarboxylic acids and/or cyclic amides thereof as defined under c2, and the branching component as defined under E, wherein an intermediate is obtained,
the removal from the intermediate of any excess of the di-ol/amine component as defined under B, and
the reaction of the intermediate with the compound as defined under D,
wherein a1, a2, and a3 are independently each used as the free dicarboxylic acid or as the dialkyl ester,
and wherein b1, b2, b3, and b4 are used underivatized as defined under b1, b2, b3, and b4,
and wherein c1 is used as the free hydroxycarboxylic acid or in the form shown in formulas IIa or IIb,

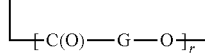

in which p is an integer from 1 to 1500 and r is an integer from 1 to 4, and G represents a radical selected from the group consisting of phenylene, $-(CH_2)_q-$, in which q is an integer from 1 to 5, $-C(R)H-$, and $-C(R)HCH_2-$, in which R is methyl or ethyl,
and wherein c2 is used as the free aminocarboxylic acids or in the form of the cyclic amide thereof,
and wherein D is used underivatized as the di- or oligoisocyanate or di- or oligoisocyanurate,
and wherein E is used underivatized.

12. The polyester of claim 1 wherein the proportion of a1 is 55 to 85 mol % and the proportion of a2 is at the same time 0 to 30 mol % and the proportion of a3 is at the same time 15 to 45 mol %.

13. The polyester of claim 1 wherein the sum of b1 and b2 is at least 50 mol %.

14. The polyester of claim 1 wherein the proportion of C in the total mass of the polyester is not more than 10% by weight.

15. The polyester of claim 2 wherein the sum of a2, b3, b4, c1, and c2, based on the total mass of the polyester, is not more than 5% by weight.

16. The polyester of claim 3 wherein b1 is selected from the group consisting of ethylene glycol, 1,4-butanediol, 1,6-hexanediol, and 1,8-octanediol.

17. The polyester of claim 4 wherein b2 is selected from the group consisting of diethylene glycol, triethylene glycol, and tetraethylene glycol.

18. The polyester of claim 5 wherein the repeat units of D have 3 to 15 carbon atoms.

19. The polyester of claim 6 wherein E are repeat units derived from the group consisting of tartaric acid, citric acid, malic acid, trimethylolpropane, pentaerythritol, and glycerol.

* * * * *